United States Patent [19]

Pawloski

[11] 3,966,768

[45] June 29, 1976

[54] SUBSTITUTED 1,3-DIOXEPINS

[75] Inventor: Chester E. Pawloski, Bay City, Mich.

[73] Assignee: The Dow Chemical Company, Midland, Mich.

[22] Filed: Jan. 22, 1973

[21] Appl. No.: 325,846

Related U.S. Application Data

[62] Division of Ser. No. 179,215, Sept. 9, 1971, Pat. No. 3,738,997, which is a division of Ser. No. 1,032, Jan. 6, 1970, Pat. No. 3,652,594.

[52] U.S. Cl. ................................. 260/338; 71/88
[51] Int. Cl.² ....................................... C07D 321/06
[58] Field of Search .................................. 260/338

[56] References Cited
UNITED STATES PATENTS 3,658,846   4/1972   Chamberlin et al. ............... 260/338

*Primary Examiner*—Norma S. Milestone
*Attorney, Agent, or Firm*—E. E. Schilling

[57] ABSTRACT

The present invention is directed to new substituted 1,3-dioxepin compounds corresponding to the formula:

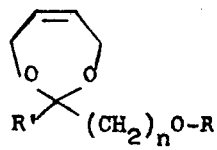

wherein R is a lower alkyl group of from 1 to about 8, both inclusive, carbon atoms or an aryl group of from 6 to about 8 carbon atoms inclusive. R' is hydrogen or an alkyl group of from 1 to about 8, both inclusive, carbon atoms, and $n$ is an integer of from 0 to about 8. The present invention is further directed to a novel process for the preparation of such substituted 1,3-dioxepin compounds wherein $n$ is 0 by reacting, at room temperatures, a corresponding trialkyl orthoalkanoate with cis-2-butene-1,4-diol in the presence of a non-oxidizing acid catalyst. The compounds of the present invention are suitable for use as herbicides.

5 Claims, No Drawings

SUBSTITUTED 1,3-DIOXEPINS

This is a division of application Ser. No. 179,215 filed Sept. 19, 1971 and now U.S. Pat. No. 3,738,997, which in turn is a division of Ser. No. 1,032, filed Jan. 6, 1970 and now U.S. Pat. No. 3,652,594.

BACKGROUND OF THE INVENTION

The present invention relates to certain novel substituted 1,3-dioxepin compounds. The known art is represented by nonanticipatory 1,3-dioxepin compounds as taught in U.S. Pat. Nos. 3,268,559; 3,116,298; and 3,116,299.

GENERAL SUMMARY

The present invention is directed to certain novel 1,3-dioxepin compounds corresponding to the formula:

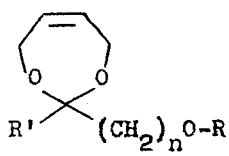

In the above and in all succeeding formulas, R is a lower alkyl group of from 1 to about 8, both inclusive, carbon atoms, or an aryl group of from 6 to about 8, inclusive, carbon atoms. R' is a hydrogen or a lower alkyl group of from 1 to about 8, both inclusive, carbon atoms, and n is an integer of from 0 to about 8.

Suitable lower alkyl groups include, for example, saturated, monovalent aliphatic radicals, including straight and branched-chain radicals of from 1 to about 8 carbon atoms, as illustrated by, but not limited to, methyl, ethyl, propyl, isopropyl, butyl, sec.-butyl, amyl, hexyl, heptyl, octyl, iso-octyl, and the like.

The term "aryl" represents phenyl, or substituted phenyl groups up to 8 carbon atoms, such as tolyl, styryl, and the like.

The new compounds are liquids at room temperature and are somewhat soluble in many common organic solvents and generally of low solubility in water. The compounds are suitable for use as herbicides.

Compounds where n is at least 1 are generally prepared by reacting a corresponding alkoxy or aryloxy acetal or ketal with cis-2-butene-1,4-diol in the presence of a non-oxidizing acid catalyst as represented below:

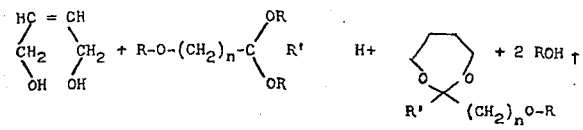

wherein R, R', and n are as hereinbefore defined.

Suitable alkoxy or aryloxy ketals operable in this process include, for example, 1-(p-tolyloxy)-2-propanone dimethyl acetal; 3-methoxy-butyraldehyde dimethyl acetal; β-ethoxy-propionaldehyde diethyl acetal and methoxy-acetaldehyde dimethyl acetal.

Any non-oxidizing acidic material of the types ordinarily employed as catalysts in organic preparations may be used in the present process. Representative operable catalysts include, for example, sulfuric acid, dichloroacetic acid, phosphoric acid, p-toluenesulfonic acid, trichloroacetic acid, dichloropropionic acid and the like.

In carrying out the preparation, the reactants are contacted with one another in any convenient manner. The reaction consumes the reactants in amounts representing essentially equimolar proportions of each and, while not critical, the use of such amounts is preferred. Usually, the reaction proceeds readily when conducted at a temperature of from about 100° to about 160° C., and when maintained for a period of time sufficient to assure completion of the reaction. Recovery of the product from the reaction mass is achieved by employing conventional procedures. Typically, the reaction mass is cooled and neutralized with a sufficient amount of a base, e.g., sodium carbonate, before being distilled at atmospheric or reduced pressures, whereupon the product is recovered as a liquid at room temperature.

Compounds where n is 0 are synthesized by a novel process which is disclosed as a part of the present invention. In this novel process cis-2-butene-1,4-diol is reacted with an appropriate trialkyl orthoalkanoate in the presence of a non-oxidizing acid catalyst according to the following reaction:

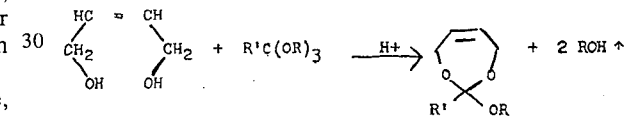

wherein R, R', and the non-oxidizing acid catalyst are as hereinbefore defined.

Representative trialkyl orthoalkanoates operable in this process include: trimethyl orthoformate; tri-n-butyl orthoformate; tri-n-amyl orthoformate; tri-methyl orthoacetate, and the like.

In a repesentative operation, the compounds are prepared by contacting the reactants with one another in any convenient manner. While the amount of the reactants utilized is not critical, a reaction whereby equimolar proportions of the reactants are employed generally results in recovery of optimum yields of the product.

Usually, the reaction proceeds at room temperature (~18°–25° C.), and ordinarily the reaction mass is agitated by a rocking or stirring motion throughout the reaction period. The reaction mass is maintained under such conditions for a period of time sufficient to assure substantial completion of the reaction. Recovery of the product from the reaction mass is achieved by employing conventional procedures. Typically, the reaction mass is cooled and neutralized with a sufficient amount of base, e.g., sodium carbonate, before being distilled at atmospheric or reduced pressure, whereupon the product is recovered as a liquid at room temperature.

DESCRIPTION OF PREFERRED EMBODIMENTS

The following examples illustrate the practice of the present invention and will enable those skilled in the art to practice the same but are not meant to limit the invention thereto.

EXAMPLE 1

2-(Methoxymethyl)-4,7-dihydro-1,3-dioxepin

60 Grams (0.5 mole) of methoxy acetaldehyde dimethyl acetal, 44 grams (0.5 mole) of cis-2-butene-1,4-diol, 0.25 grams of p-toluenesulfonic acid as catalyst, and 100 milliliters of benzene weere mixed. This mixture was distilled under normal atmospheric conditions until a temperature of 153° C. was observed. After the residual reaction mass was cooled and neutralized by adding a sufficient amount of sodium carbonate, the reaction mass was further distilled at atmospheric pressure. The 2-(methoxymethyl)-4,7-dihydro-1,3-dioxepin compound was recovered from this latter distillation. This product was a liquid at room temperature and had a boiling point of 103° C. at an absolute pressure of 3.5 millimeters of Hg; its index of refraction ($n_D^{25}$) was 1.4566. The assigned structure was substantiated by infrared spectroscopy analysis.

EXAMPLE 2

2-(β-Ethoxyethyl)-4,7-dihydro-1,3-dioxepin

50 Grams (0.28 mole) of β-ethoxy propionaldehyde diethyl acetal, 25 grams (0.28 mole) cis-2-butene-1,4-diol, 2 drops of concentrated sulfuric acid as catalyst, and 100 milliliters of benzene were mixed and the reaction mass distilled under normal atmospheric pressure until a temperature of 112° C. was observed. The residual reaction mass was cooled and neutralized by the addition of a sufficient amount of sodium carbonate before further distillation. The 2-(ethoxyethyl)-4,7-dihydro-1,3-dioxepin compound was recovered from this latter distillation. This product was a liquid at room temperature, and had a boiling point of 90° C. at an absolute pressure of 4.5 millimeters of Hg. Its assigned structure was confirmed by infrared spectroscopy analysis.

EXAMPLE 3

2-(2-Methoxypropyl)-4,7-dihydro-1,3-dioxepin

50 Grams (0.34 mole) of 3-methoxy butyraldehyde dimethyl acetal, 38 grams (0.34 mole) of cis-2-butene-1,4-diol, 0.25 grams of p-toluenesulfonic acid as catalyst, and 100 milliliters of benzene were reacted and distilled at atmospheric pressure until a temperature of 109° C. was observed. The residual reaction mass was cooled and neutralized by the addition of a sufficient amount of sodium carbonate and then further distilled. The 1,3-dioxepin product was recovered from this latter distillation as the distillate. Analysis by infrared spectroscopy methods confirmed that the product mass was substantially 2-(2-methoxypropyl)-4,7-dihydro-1,3-dioxepin having some unsaturated 1,3-dioxepin compounds in admixture therewith.

EXAMPLE 4

2-Methyl-2-(p-tolyloxymethyl)-4,7-dihydro-1,3-dioxepin

Following the same general procedures set forth in Example 1, 25 grams (0.125 mole) of 1-(p-tolyloxy)-2-propanone dimethyl acetal, 11 grams (0.125 mole) of cis-2-butene-1,4-diol, one drop of concentrated sulfuric acid as catalyst, and 100 milliliters benzene were mixed and distilled until a temperature of 130° C. was observed. The residual reaction mass was cooled and neutralized by the addition of a sufficient amount of sodium carbonate before further distillation. Final distillation under reduced atmospheric pressure resulted in the recovery of the 2-methyl-2-(p-tolyloxymethyl)-4,7-dihydro-1,3-dioxepin compound as a liquid at room temperature. The recovered compound had a boiling point of 128° C. at an absolute pressure of 0.6 millimeter of Hg; its index of refraction ($n_D^{25}$) was 1.5248. The assigned structure was substantiated by infrared spectroscopy analysis.

In procedures analogous to the foregoing and in accordance with the method of the present invention, the following compounds of the present invention, where $n$ is at least 1, are prepared:

2-Butyl-2-(butoxyheptyl)-4,7-dihydro-1,3-dioxepin (m.w. 326) by reacting together 12-butoxy-5-dodecanone dimethyl acetal and cis-2-butene-1,4-diol.

2-Ethyl-2-(octyloxypentyl)-4,7-dihydro-1,3-dioxepin (m.w. 326) by reacting together 8-octyloxy-3-octanone dimethyl acetal and cis-2-butene-1,4-diol.

2-Hexyl-2-(hexyloxyoctyl)-4,7-dihydro-1,3-dioxepin (m.w.) 396) by reacting together 15-hexyloxy-7-pentadecanone dimethyl acetal and cis-2-butene-1,4-diol.

2-Octyl-2-(ethoxyethyl)-4,7-dihydro-1,3-dioxepin (m.w. 284) by reacting together 1-ethoxy-3-undecanone dimethyl acetal and cis-2-butene-1,4-diol.

2-(Phenoxymethyl)-4,7-dihydro-1,3-dioxepin (m.w. 205) by reacting together phenoxy acetaldehyde dimethyl acetal and cis-2-butene-1,4-diol.

2-(Styryloxymethyl)-4,7-dihydro-1,3-dioxepin (m.w. 232) by reacting together styryloxy acetaldehyde dimethyl acetal and cis-2-butene-1,4-diol.

2-(p-Ethylphenoxy methyl)-4,7-dihydro-1,3-dioxepin (m.w. 234) by reacting together p-ethylphenoxy acetaldehyde dimethyl acetal and cis-2-butene-1,4-diol.

EXAMPLE 5

2-Methoxy-4,7-dihydro-1,3-dioxepin

106 Grams (1.0 mole) of trimethyl orthoformate, 80 grams (0.9 mole) of cis-2-butene-1,4-diol, and 4 drops of concentrated sulfuric acid as catalyst were contacted and the reaction mass stirred for two hours at room temperature. The reaction mass was neutralized by adding a sufficient amount of sodium carbonate and then distilled under normal atmospheric pressure. The 2-methoxy-4,7-dihydro-1,3-dioxepin compound was recovered from the distillation as a liquid at room temperature. This product had a boiling point of 48° C. at an absolute pressure of 4.2 millimeters of Hg. The structure was confirmed by infrared spectroscopy analysis.

EXAMPLE 6

2-Butoxy-4,7-dihydro-1,3-dioxepin

25 Grams (0.108 mole) of tri-n-butyl orthoformate, 9 grams (0.1 mole) of cis-2-butene-1,4-diol, and one drop of concentrated sulfuric acid as catalyst were mixed and stirred for five hours at room temprature. The resulting single-phase mixture was neutralized by the addition of a sufficient amount of sodium carbonate. Distillation under normal atmospheric pressure was carried out and the 2-butoxy-4,7-dihydro-1,3-dioxepin compound was recovered as a liquid at room temperature. The recovered product had an index of refraction ($n_D^{25}$) of 1.4435. Its structure was confirmed by infrared spectroscopy analysis.

EXAMPLE 7

2-Amyloxy-4,7-dihydro-1,3-dioxepin

70 Grams (0.25 mole) of tri-n-amyl orthoformate, 22 grams (0.25 mole) of cis-2-butene-1,4-diol, and 2 drops of concentrated sulfuric acid as catalyst were mixed and stirred for 4 hours at room temperature. A single-phase mixture was obtained which was neutralized by the addition of a sufficient amount of sodium carbonate before distillation under normal atmospheric conditions. The 2-amyloxy-4,7-dihydro-1,3-dioxepin compound was recovered from the distillation as a liquid at room temperature. The product had a boiling point of 79° C. at an absolute pressure of 1 millimeter of Hg pressure. Its structure was confirmed with the use of infrared spectroscopy analysis methods.

EXAMPLE 8

2-Methoxy-2-methyl-4,7-dihydro-1,3-dioxepin

60 Grams (0.5 mole) of trimethyl orthoacetate, 42 grams (0.48 mole) of cis-2-butene-1,4-diol, and 2 drops of concentrated sulfuric acid as catalyst were mixed and stirred as in Example 3. Neutralization and distillation were also carried out as in Example 3, and the 2-methoxy-2-methyl-4,7-dihydro-1,3-dioxepin compound was recovered as a liquid at room temprature. The product had a boiling point of 44° C. at an absolute pressure of 2.8 millimeters of Hg; its index of refraction ($n_D^{25}$) was 1.4520. Its structure was also confirmed by infrared spectroscopy analysis.

In procedures analogous to the foregoing and in accordance with the method of the present invention, the following compounds of the present invention, where *n* is 0, are prepared:

2-Ethoxy-4,7-dihydro-1,3-dioxepin (m.w. 144) by reacting together triethyl orthoformate and cis-2-butene-1,4-diol.

2-Ethoxy-2-ethyl-4,7-dihydro-1,3-dioxepin (m.w. 172) by reacting together triethyl orthopropionate and cis-2-butene-1,4-diol.

2-Hexyloxy-2-propyl-4,7-dihydro-1,3-dioxepin (m.w. 242) by reacting together trihexyl orthobutyrate and cis-2-butene-1,4-diol.

2-Octyloxy-2-heptyl-4,7dihydro-1,3-dioxepin (m.w. 326) by reacting toether trioctyl orthooctanoate and cis-2-butene-1,4-diol.

2-Styryloxy-2-amyl-4,7-dihydro-1,3-dioxepin (m.w. 288) by reacting together tristyryl orthohexanoate and cis-2-butene-1,4-diol.

2-Tolyloxy-2-octyl-4,7-dihydro-1,3-dioxepin (m.w. 318) by reacting together tritolyl orthononanoate and cis-2-butene-1,4-diol.

The compounds of the present invention are suitable for use as herbicides. When the product is so employed, the unmodified substance can be utilized. However, the present invention also embraces the use of the compound in a formulation. Thus, for example, the compound can be dispersed in a finely divided solid and employed therein as a dust. Also, the compound, or a solid composition comprising the compound, can be dispersed in water, typically with the aid of a wetting agent, and the resulting aqueous suspension employed as a spray. In other procedures, the compound can be employed as a constituent of organic liquid compositions, oil-in-water and water-in-oil emulsions, or water dispersions, with or without the addition of wetting, dispersing, or emulsifying agents.

In a representative operation, application of 10 pounds per acre of the 2-(ethoxyethyl)-4,7-dihydro-1,3-dioxepin, 2-(methoxymethyl)-4,7dihydro-1,3-dioxepin, and 2-methoxy-4,7dihydro-1,3-dioxepin compounds gave complete inhibition of pigweeds.

The acetal and ketal starting materials used in preparing compounds where n is at least 1 can be obtained from commercial sources or prepared by converting aldehydes to acetals with various alcohols in a conventional manner. (See for example Wertheim, "Textbook of Organic Chemistry", 2nd Ed., p. 144, The Blakeston Company (1945)).

The ketal starting materials are also available commercially and can be prepared through the reaction of ketones with an alkyl orthoformate compound in the presence of an acid catalyst. (See for example Roberts and Caserio, "Basic Principles of Organic Chemistry", p. 447–448, (1965), W. A. Benjamin, Inc.). To illustrate, 1-p-Tolyloxy-2-propanone dimethylacetal is prepared as follows:

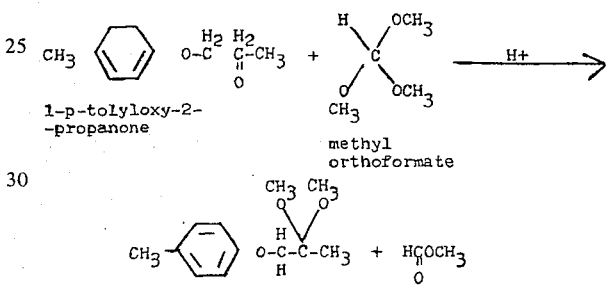

Starting materials of the formula R'C(OR)$_3$ used in preparing the compounds wherein *n* is 0 are available commercially or may be synthesized. Ethyl orthoformate, for example, is prepared by reacting chloroform with sodium ethoxide, and other starting materials are similarly prepared by utilizing this method with the appropriate chemical analogs.

I claim:

1. Substituted 1,3-dioxepin compounds corresponding to the formula:

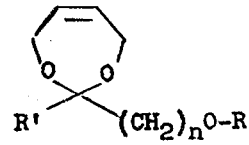

wherein R is a lower alkyl group of from 1 to about 8 carbon atoms, inclusive; R' is hydrogen or a lower alkyl group of from 1 to about 8 carbon atoms, inclusive; and *n* is an integer of from 1 to about 8.

2. The compound of claim 1 which is 2-(methoxymethyl)-4,7-dihydro-1,3-dioxepin.

3. The compound of claim 1 which is 2(β-ethoxyethyl)-4,7-dihydro-1,3-dioxepin.

4. The compound of claim 1 which is 2-(2-methoxypropyl)-4,7-dihydro-1,3-dioxepin.

5. The composition of claim 1 wherein R' is hydrogen, R is a lower alkyl group of 1 to 8 carbon atoms inclusive; and *n* is an integer of from 1 to 8.

* * * * *

UNITED STATES PATENT AND TRADEMARK OFFICE
CERTIFICATE OF CORRECTION

PATENT NO. : 3,966,768
DATED : June 29, 1976
INVENTOR(S) : Chester E. Pawloski

It is certified that error appears in the above-identified patent and that said Letters Patent are hereby corrected as shown below:

Column 1, after the title of the invention, the paragraph title, "Cross-Reference to Related Application" has been omitted.

Column 1, line 4, "Sept. 19, 1971" should read -- Sept. 9, 1971 --.

Column 3, line 7, "weere" should read -- were --.

Column 4, line 21, "(m.w.)" should read -- (m.w. --.

Column 4, line 60, "temprature" should read -- temperature --.

Column 5, line 27, "temprature" should read -- temperature --.

Column 5, line 46, "toether" should read -- together --.

Column 6, line 3, "2-(methoxymethyl)-4,7dihydro-1,3-" should read -- 2-(methoxymethyl)-4,7-dihydro-1,3- --.

Column 6, line 4, "2-methoxy-4,7dihydro-1,3-dioxepin" should read -- 2-methoxy-4,7-dihydro-1,3-dioxepin --.

Column 6, line 61, Claim 3, "which is 2(β-ethoxye -" should read -- which is 2-(β-ethoxye- --.

Signed and Sealed this

Fifth Day of April 1977

[SEAL]

Attest:

RUTH C. MASON
*Attesting Officer*

C. MARSHALL DANN
*Commissioner of Patents and Trademarks*